United States Patent
Wang et al.

(10) Patent No.: US 8,115,502 B2
(45) Date of Patent: Feb. 14, 2012

(54) FLUID MEASURING APPARATUS

(75) Inventors: William Wang, Taoyuan (TW); Chung-Cheng Chou, Lujhu Township (TW)

(73) Assignee: Raydium Semiconductor Corporation, Hsinchu (TW)

( * ) Notice: Subject to any disclaimer, the term of this patent is extended or adjusted under 35 U.S.C. 154(b) by 436 days.

(21) Appl. No.: 12/336,836

(22) Filed: Dec. 17, 2008

(65) Prior Publication Data
US 2009/0167328 A1    Jul. 2, 2009

(30) Foreign Application Priority Data
Dec. 28, 2007   (TW) ................................ 96150752 A (51) Int. Cl.
*G01R 27/08*    (2006.01)
(52) U.S. Cl. ........................................................ 324/701
(58) Field of Classification Search .................. None
See application file for complete search history.

(56) References Cited

U.S. PATENT DOCUMENTS

| | | | | |
|---|---|---|---|---|
| 3,451,741 A | * | 6/1969 | Manos ........................ 359/275 |
| 4,212,202 A | * | 7/1980 | Schmidt ...................... 73/304 C |
| 4,994,167 A | * | 2/1991 | Shults et al. ............. 204/403.05 |
| 5,120,420 A | * | 6/1992 | Nankai et al. ............ 204/403.11 |
| 5,469,749 A | * | 11/1995 | Shimada et al. ........... 73/861.47 |
| 6,553,830 B2 | * | 4/2003 | Fahrenbach et al. .......... 324/637 |
| 6,849,052 B2 | * | 2/2005 | Uchigaki et al. .............. 600/584 |
| 7,252,804 B2 | * | 8/2007 | Miyashita et al. ............ 600/573 |
| 7,533,566 B2 | * | 5/2009 | Tung et al. .................... 324/658 |
| 7,772,855 B2 | * | 8/2010 | Sakuma et al. ............... 324/693 |
| 2004/0133125 A1 | * | 7/2004 | Miyashita et al. ............ 600/573 |

* cited by examiner

*Primary Examiner* — Jermele M Hollington
(74) *Attorney, Agent, or Firm* — Morris Manning & Martin LLP; Tim Tingkang Xia, Esq.

(57) ABSTRACT

The invention provides a fluid measuring apparatus, which includes a collector, a sensing circuit, and an electrochromic device electrically connected to the sensing circuit. When the concentration of a fluid flowing through the collector and between the sensing circuit varies, the color of the electrochromic device changes accordingly. Further, the electrochromic device includes an electrochromic material, and the sensing circuit includes a first electrode and a second electrode, wherein the first and the second electrodes are disposed in the collector and the electrochromic material is disposed on the first electrode. When the concentration of an electrolytic solution flowing between the first electrode and the second electrode varies, the color of the electrochromic material changes accordingly.

19 Claims, 5 Drawing Sheets

FLUID MEASURING APPARATUS

CROSS-REFERENCE TO RELATED APPLICATIONS

This non-provisional application claims priority under 35 U.S.C. §119(a) on Patent Application No. 096150752 filed in Taiwan, R.O.C. on Dec. 28, 2007, the entire contents of which are hereby incorporated by reference.

BACKGROUND OF THE INVENTION

1. Field of the Invention

This present invention relates to a fluid measuring apparatus, and more particularly relates to a fluid measuring apparatus utilizing an electrochromic material.

2. Description of the Prior Art

In the field of measuring fluid concentration, one of typical applications is particle counting. A common method thereof is to calculate the quantity of particles in a fluid by directly measuring the current flowing through the fluid containing the particles. Another common method thereof is to utilize other chemical matter to react with particles in a fluid first, then to get a fluorescence reaction generated by radiating, and at last to perform image capturing and image judgment in turn to obtain the quantity of the particles in the fluid. In the former method, the quantity of the particles is still needed to be calculated by the flowing-through current, so a user cannot judge the quantity of the particles in the fluid by directly measuring the current. In the latter method, the particles has been reacted, which is a semi-destructive counting method; therefore, it is not suitable for any case. Furthermore, the judgement process is long, and additional instruments are needed, so it is indeed unsuitable for a case required of quick judgments.

Therefore, there is a need to provide a new fluid measuring apparatus which can allow users to directly and quickly make a judgment to solve the above problems.

SUMMARY OF THE INVENTION

A scope of the invention is to provide a fluid measuring apparatus utilizing an electrochromic material.

A fluid measuring apparatus of the invention includes a collector, a first sensing circuit, and a first electrochromic device. The collector includes a first cavity, an inlet, and an outlet. The first cavity includes a first inner wall and a second inner wall. A fluid is allowed to flow into the first cavity through the inlet and then flows out of the first cavity through the outlet. The first sensing circuit includes a first electrode disposed on the first inner wall and a second electrode disposed on the second inner wall. The first electrochromic device is electrically connected to the first sensing circuit, such as in parallel or in series, even in parallel directly with the first electrode and the second electrode. The first electrochromic device is directly attached onto a surface of the collector corresponding to the first cavity. When the first sensing circuit is enabled and then the concentration of the fluid flowing through between the first electrode and the second electrode varies, the color of the first electrochromic device will get changed. Therefore, a user could judge the concentration of the fluid by directly inspecting the change of the color of the first electrochromic device. Further, if the fluid contains particles, the quantity of the particles could also be judged.

The fluid measuring apparatus of the invention further includes a second sensing circuit, which includes a third electrode disposed on the first inner wall and a fourth electrode disposed on the second inner wall. In the first cavity, a first inspection room is defined between the first electrode and the second electrode, and a second inspection room is defined between the third electrode and the fourth electrode. In this case, the fluid measuring apparatus also includes a second electrochromic device electrically connected to the second sensing circuit. The second electrochromic device is disposed on a surface of the collector corresponding to the second inspection room, while the first electrochromic device is disposed on a surface of the collector corresponding to the first inspection room. Thereby, a user could easily judge the quantities of the particles in the different inspection rooms, which is suitable for measuring not only the flowing particles but also the accumulated particles.

For example, when the first cavity is designed as a room for accumulating particles, a user could easily judge the change of the particles accumulated in the first cavity by the color changes of the electrochromic devices corresponding to the inspection rooms. The accumulation of the particles could be realized by controlling the aperture of the inlet and the aperture of the outlet. The particles whose size is between the aperture of the inlet and the aperture of the outlet will be accumulated in the first cavity. It is certain that the aperture of the inlet is larger than the aperture of the outlet. The sieving function of the outlet could also be realized by a filter, such as a screen, and the mesh of the screen will replace the aperture of the outlet. Similarly, the sieving function of the inlet could also be realized by a filter in order to accumulate particles whose size is within a specific range. If the fluid measuring apparatus of the invention is made in a chip-level manufacturing, the filter could be integrated into the manufacturing without any added components. Furthermore, the aperture of the filter could be easily made in nano-scale.

In addition, the first electrochromic device has a first colored-state color, and the second electrochromic device has a second colored-state color. A user could identify and judge the quantity of the particles in different inspection rooms easily based on that the first colored-state color is different to the second colored-state color.

The fluid measuring apparatus of the invention could further include a third sensing circuit, a third electrochromic device, and a second cavity. The second cavity also includes an inlet, an outlet, a third inner wall, and a fourth inner wall. The fluid is also allowed to flow through the second cavity. The third sensing circuit includes a fifth electrode disposed on the third inner wall and a sixth electrode disposed on the fourth inner wall. The third electrochromic device is disposed on a surface of the collector corresponding to the second cavity and is electrically connected to the third sensing circuit. Similarly, when the third sensing circuit is enabled, the color of the third electrochromic device changes correspondingly if the concentration of the fluid flowing through between the fifth electrode and the sixth electrode varies.

The second cavity could be structurally connected to the first cavity in parallel to inspect the particles respectively. The second cavity could also be structurally connected to the first cavity in series, that is, the outlet of the second cavity is connected to the inlet of the first cavity. When both the first cavity and the second cavity are designed as rooms for accumulating particles, the first cavity and the second cavity could respectively accumulate the particles of different ranges. In a case of accumulating the particles within continual ranges, the aperture of the inlet of the first cavity is substantially equal to the aperture of the outlet of the second cavity. The above description regarding the inlet and the outlet of the first cavity can also be applied to the second cavity, which is no longer described here.

Another fluid measuring apparatus of the invention includes a collector, a first electrode, a second electrode, and an electrochromic device. The collector includes a cavity, an inlet, and an outlet. The cavity includes a first inner wall and a second inner wall. The first electrode is disposed on the first inner wall. The second electrode is disposed on the second inner wall. The electrochromic device includes an electrochromic material disposed on the first electrode. An electrolytic solution flows into the cavity through the inlet and flows out of the cavity through the outlet. When there is a voltage difference between the first electrode and the second electrode and the concentration of the electrolytic solution flowing through between the first electrode and the second electrode varies, the color of the electrochromic material will get changed accordingly. In one embodiment, the electrolytic solution includes an ion for generating an electrochemical reaction with the electrochromic material. When there is a voltage difference between the first electrode and the second electrode, the ion is impelled to react with the electrochromic material so that the color of the electrochromic material changes. In another embodiment, the ion is provided by an ion storage layer. The ion storage layer is disposed on the second electrode. When there is a voltage difference between the first electrode and the second electrode, the ion is impelled to pass through the electrolytic solution to react with the electrochromic material so that the color of the electrochromic material changes.

Because the electrochromic material is disposed in the cavity and is shaded by the first electrode, the color change of the electrochromic material is observed hardly. Therefore, a transparent electrode is needed or the first electrode is holed partially, so that the color change of the electrochromic material could be observed. Certainly, the collector is made of transparent material or holed partially accordingly, so that the color changes of the electrochromic material could be observed.

The previous descriptions of the first cavity and the second cavity of the fluid measuring apparatus can also be applied here. For example, the cavity here could also accumulate the particles of a specific range by controlling the apertures of both the outlet and the inlet of the cavity, or another cavity is further included to be connected to the current cavity in series. It is no longer described here.

It is added that, whichever of the fluid measuring apparatuses of the invention needs a power circuit for powering both the first electrode and the second electrode or both the sensing circuits and the electrochromic devices. The power circuit could be an external power or a built-in power, such as battery. If the power circuit is a built-in power, the fluid measuring apparatus of the invention is convenient to be carried. Then, the function of counting particles quickly and largely can be realized.

As described above, the fluid measuring apparatus of the invention utilizes the electrochromic material whose color changes based on that the concentration of the fluid in the collector varies so as to influence the electrochemical reaction thereof, so that a user could estimate the quantity of the particles in the fluid accordingly. Since the user directly faces the colors which are easily identified by human eyes, not current values, even without following fluorescence and image analysis, the fluid measuring apparatus of the invention has the property of rapidity which does not exist in conventional particle-counting apparatuses. The degree of the color change of the electrochromic material is relative to the concentration of the fluid, that is, the color of the electrochromic material has difference of depth, which is conducive to the estimation of the concentration of the fluid or the quantity of the particles for the user. In addition, by configuring several inspection rooms disposed with corresponding electrochromic devices in series, the fluid measuring apparatus of the invention could also provide a colored-bar display effect, which is more conducive to the estimation of the quantity of the particles in the fluid.

The advantage and spirit of the invention may be understood by the following recitations together with the appended drawings.

DETAILED DESCRIPTION OF THE INVENTION

Figure 1:
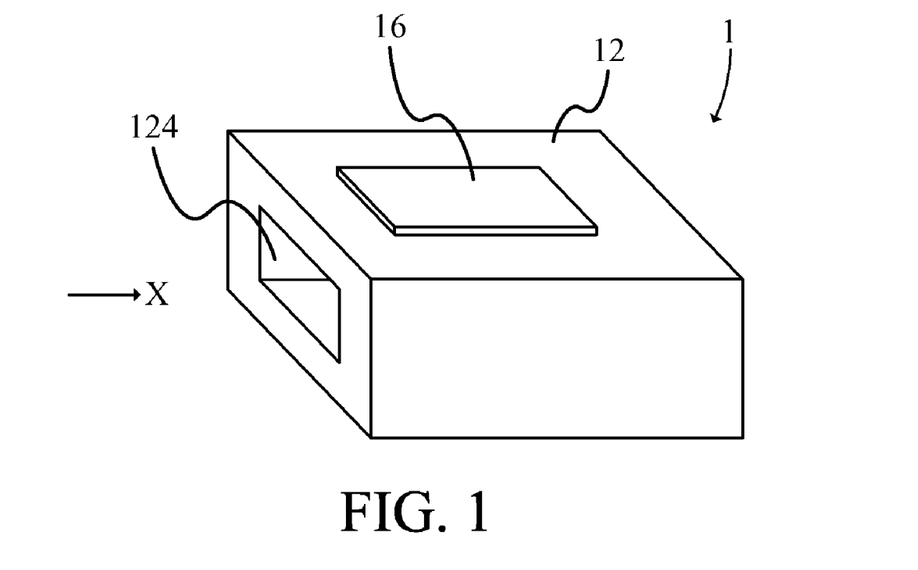
FIG. 1 is a sketch diagram illustrating a fluid measuring apparatus of the invention according to a preferred embodiment.
Figure 2:
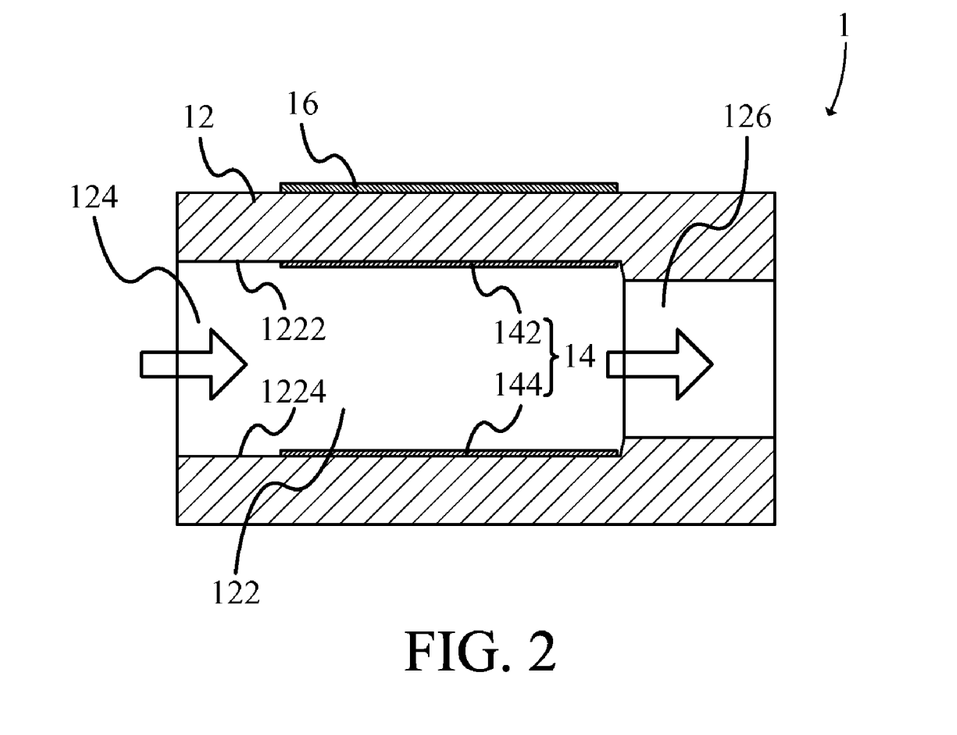
FIG. 2 is a cross section of the fluid measuring apparatus along the direction X in FIG. 1.

Please refer to FIG. 1 and FIG. 2. FIG. 1 is a sketch diagram illustrating a fluid measuring apparatus 1 of the invention according to a preferred embodiment. FIG. 2 is a cross section of the fluid measuring apparatus 1 along the direction X in FIG. 1. The fluid measuring apparatus 1 of the invention includes a collector 12, a sensing circuit 14, and an electrochromic device 16. The collector 12 includes a cavity 122, an inlet 124, and an outlet 126. The cavity 122 includes a first inner wall 1222 and a second inner wall 1224. The sensing circuit 14 includes a first electrode 142 disposed on the first inner wall 1222 and a second electrode 144 disposed on the second inner wall 1224. The electrochromic device 16 is electrically connected to the sensing circuit 14. The electrochromic device 16 is disposed on a surface of the collector 12 corresponding to the cavity 122, but the invention is not limited to this. The electrochromic device 16 could also be disposed on the spot which is easy for users to observe. The hollow arrow in FIG. 2 indicates the following path of a fluid containing particles. When the sensing circuit 14 is enabled and then the concentration of the fluid flowing through and between the first electrode 142 and the second electrode 144 varies, the color of the first electrochromic device 16 will be changed. It is added that the first inner wall 1222 and the second inner wall 1224 of the fluid measuring apparatus 1 of the invention are not necessary to be disposed opposite.

Figure 3A:
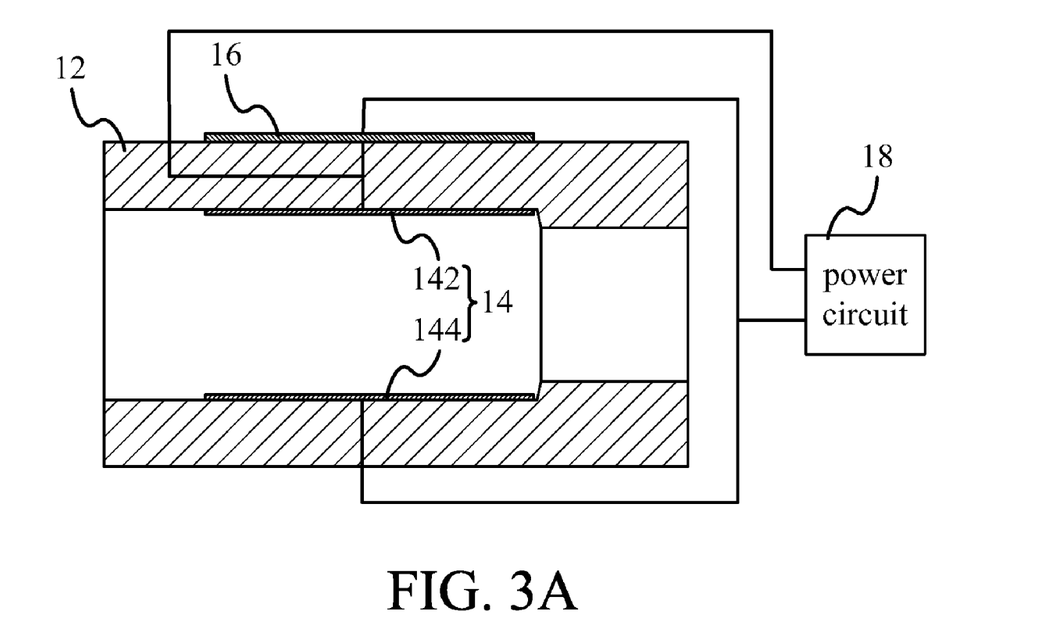
FIG. 3A is a sketch diagram illustrating the parallel connection of the electrochromic device and the sensing circuit.
Figure 3B:
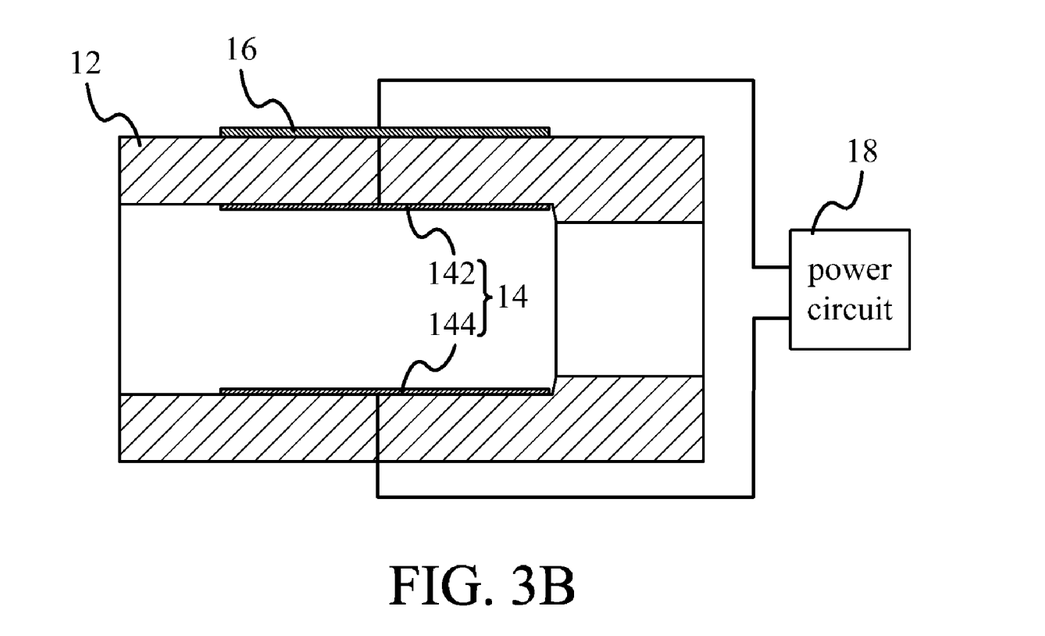
FIG. 3B is a sketch diagram illustrating the series connection of the electrochromic device and the sensing circuit.

Please refer to FIGS. 3A and 3B. FIG. 3A is a sketch diagram illustrating the parallel connection of the electrochromic device 16 and the sensing circuit 14. FIG. 3B is a sketch diagram illustrating the series connection of the electrochromic device 16 and the sensing circuit 14. The connection lines in figures refer to the logical connection, not the physical connection. As shown in the figures, the fluid measuring apparatus 1 of the invention further includes a power circuit 18 for powering the electrodes 142 and 144 and the electrochromic device 16. The power of the power circuit 18 could be supplied by a built-in battery or by an external power source. When a built-in power is utilized, the fluid measuring apparatus 1 of the invention has the property of mobility, which is conducive to quick and large measurement. In addition, the connection shown in the figures is logical, so there could be other electronic components among the power circuit 18, the first electrode 142, the second electrode 144, and the electrochromic device 16 for fine tuning and setting the electrical relation between the electrochromic device 16 and the sensing circuit 14 (especially the first electrode 142 and the second electrode 144). For example, a voltage difference between the first electrode 142 and the second electrode 144 is set to be large so as to gain a better sensitivity. However, the electrochromic device 16 connected to the first electrode 142 and the second electrode 144 in parallel may not or need not sustain such voltage difference, and then a resistance could be added at an end of the electrochromic device 16 for reducing the voltage difference the electrochromic device 16 sustains; vice versa. Furthermore, the sensing circuit 14 could also have other circuit designs for controlling the electrical characteristics between the first electrode 142 and the second electrode 144.

Figure 4:
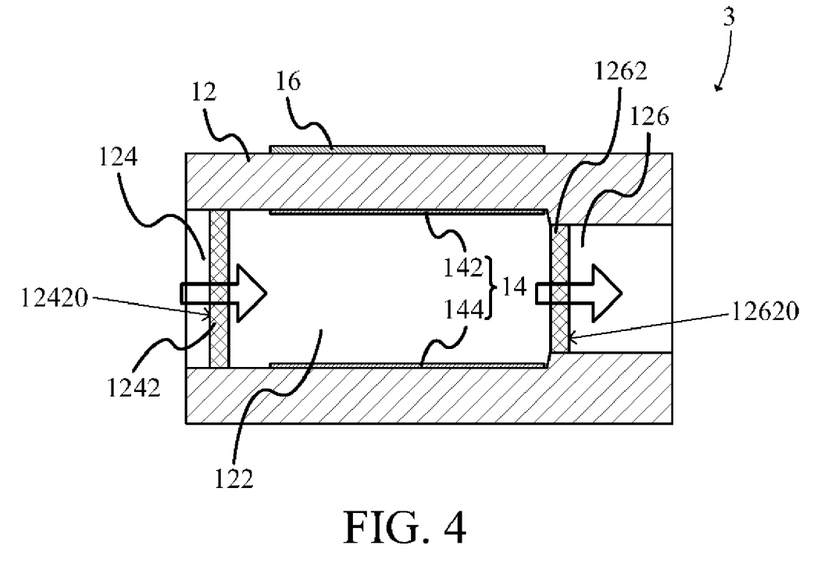
FIG. 4 is a cross section of a fluid measuring apparatus of the invention with filters according to another preferred embodiment.

Please refer to FIG. 4. FIG. 4 is a cross section of a fluid measuring apparatus 3 of the invention with filters according to another preferred embodiment. Compared with the fluid measuring apparatus 1, the difference is that the fluid measuring apparatus 3 includes filters 1242 and 1262 at the inlet 124 and the outlet 126 respectively, such as screen. The filter 1242 has a first aperture 12420, and the filter 1262 has a second aperture 12620. The first aperture 12420 is larger than the second aperture 12620. Therefore, the cavity 122 could accumulate the particles whose size is between the second aperture 12620 and the first aperture 12420. If the fluid measuring apparatus 3 only has the filter 1242 disposed at the inlet 124, the particle size of the particles inspected by the fluid measuring apparatus 3 is smaller than the first aperture 12420. Similarly, if the fluid measuring apparatus 3 only has the filter 1262 disposed at the outlet 126, the particle size of the particles accumulated by the fluid measuring apparatus 3 is larger than the second aperture 12620.

In addition, if the collector 12 is made in a chip-level manufacturing, the filters 1242 and 1262 could be integrated into the manufacturing. For example, etching a half cavity on a substrate, and then etching at least one groove at both a corresponding inlet and a corresponding outlet. The previous process is also performed on another substrate. At last, the two substrates are connected opposite, so that the two half cavities are formed to be the cavity 122 of the invention and the grooves are formed to be the inlet 124 and the outlet 126 respectively. The apertures formed by the grooves after the connection are the apertures of the inlet 124 and the outlet 126. Based on the above manufacturing, the whole cross section of the inlet 124 is not necessary to be larger than the whole cross section of the outlet 126, but the aperture formed by the grooves at the inlet 124 needs to be larger than the aperture formed by the grooves at the outlet 126, which also can be applied to the case of utilizing the filters 1242 and 1262. Therefore, the grooves perform the same effect as the filters 1242 and 1262.

Furthermore, in the above-mentioned manufacturing, the electrodes 142 and 144 and the electrochromic device 16 could also be formed together, such as by plating, depositing, or coating. In addition, a preliminary electrical connection could be performed at the same manufacturing. Because the manufacturing could be easily performed in nano-scale, not only could the above-mentioned apertures be easily formed in nano-scale, but the cavity 122 could also be a cavity of nano-scale. Therefore, the fluid measuring apparatus of the invention could be made in a chip, which expands the application. It is added that if the cross section of the cavity 122 has the same sieving function as the apertures formed by the above-mentioned grooves, the grooves at the above inlet 124 could be omitted. However, considering a large sum of particles counting, the cavity 122 needs a long and narrow room.

In the fluid measuring apparatus 1 of the invention, because the difference of the quantity of the particles in the cavity 122 leads to the difference of the concentration of the fluid in the cavity 122 (in the room between the first electrode 142 and the second electrode 144), the electrical conductivity of the fluid differs. The electrical relation between the first electrode 142 and the second electrode 144 reflects to the electrochromic device 16 electrically connected to the electrodes 142 and 144, so that the electrochromic material of the electrochromic device 16 reacts to induce color-changing effect based on the terminal voltage loaded on the electrochromic device 16. In principle, the electrochromic device 16 has only one colored-state color, but the quantity of the reaction (such as the magnitude of current) with the electrochromic material will influence the changes of the colored-state color (from dark to light). That is, a user could estimate the quantity of the particles based on the change degree of the colored-state color of the electrochromic device 16. In order for a user to speed up the comparison of the relation between the change degree of the colored-state color and the quantity of the particles, a color table is pasted on the collector 12 with the electrochromic device 16, so that the user could compare with the color table to estimate the quantity of the particles quickly.

Figure 5:
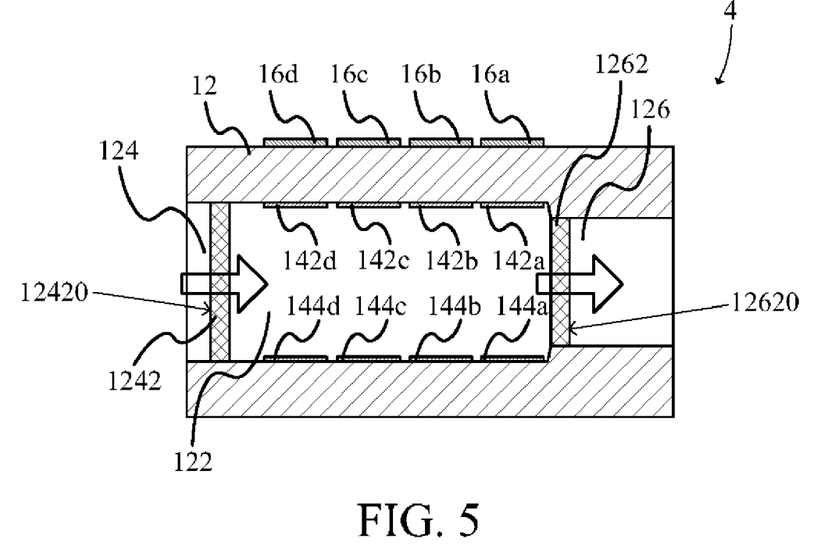
FIG. 5 is a cross section of a fluid measuring apparatus of the invention with several sets of electrodes according to another preferred embodiment.

Please refer to FIG. 5. FIG. 5 is a cross section of a fluid measuring apparatus 4 of the invention with several sets of electrodes according to another preferred embodiment. Compared with the fluid measuring apparatus 3, the difference is that the fluid measuring apparatus 4 includes several electrodes 142*a-d* ad 144*a-d* and several electrochromic devices 16*a-d*. Each of the electrochromic devices 16*a-d* corresponds to a set of the electrodes 142*a-d* and 144*a-d*. An inspection room is defined between each set of the electrodes 142*a-d* and 144*a-d*. In principle, each set of the electrodes 142*a-d* and 144*a-d* is mainly influenced by its corresponding inspection room. Each of the electrochromic devices 16*a-d* is disposed on a surface of the collector 12 corresponding to the corresponding inspection room, which could provide a bar-scale display for users. The electrochromic devices 16*a-d* are not necessary to be disposed coplanarly, and the surfaces where the electrochromic devices 16*a-d* are disposed are not limited to be the same surface. As shown in FIG. 5, the fluid measuring apparatus 4 includes filters 1242 and 1262; therefore, the cavity 122 has a function of accumulating the particles whose size is within a specific range. Because the degree of accumulating particles in the cavity 122 reflects on the electrochromic devices 16*a-d* corresponding to the inspection rooms, the user could quickly judge the quantity of the particles based on the display of the bar-scale display induced by the electrochromic devices 16*a-d*. In addition, each of the electrochromic devices 16a-d is not necessary to be the same. For example, each of the electrochromic devices 16a-d has its own colored-state color, and all colored-state colors are different, too. Thereby, the display of the bar-scale display induced by the electrochromic devices 16a-d is more helpful for users to make a judgment.

Figure 6:
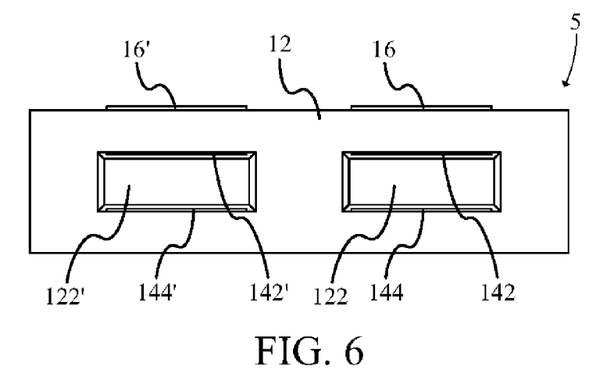
FIG. 6 is a sketch diagram illustrating a fluid measuring apparatus of the invention with two cavities disposed in parallel according to another preferred embodiment.

Please refer to FIG. 6. FIG. 6 is a sketch diagram illustrating a fluid measuring apparatus 5 of the invention according to another preferred embodiment. FIG. 6 is a sketch diagram of the fluid measuring apparatus 5 along the direction X in FIG. 1. The fluid measuring apparatus 5 includes two cavities 122 and 122' in a row. There are two electrochromic devices 16 and 16' disposed on a surface of the collector 12 corresponding to the cavities 122 and 122'. Moreover, there are two sets of the electrodes, namely a first electrode 142, a second electrode 144, a third electrode 142', and a forth electrode 144' disposed on the inner walls. The relations among the above-mentioned components are similar to those in the previously mentioned embodiments, which is no longer described here. In the fluid measuring apparatus 5, the two cavities 122 and 122' perform counting respectively. In a case of arranging several cavities in a row, the counting could be accelerated.

Figure 7:
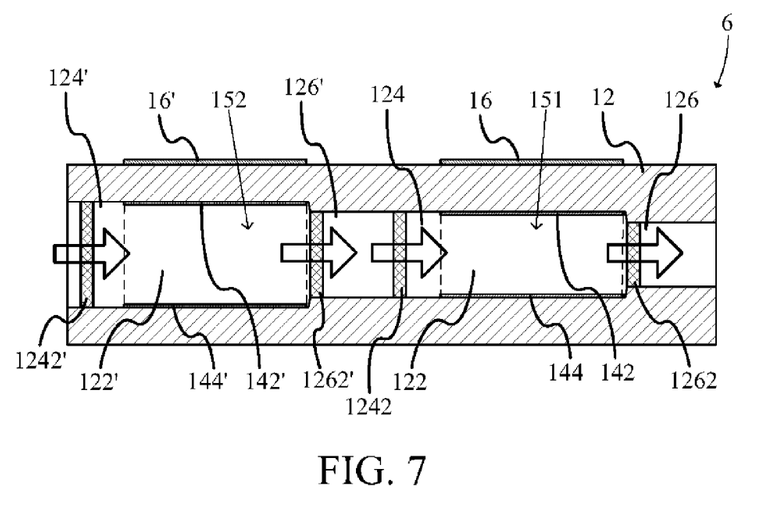
FIG. 7 is a cross section of a fluid measuring apparatus of the invention with two cavities disposed in series according to another preferred embodiment.

Please refer to FIG. 7. FIG. 7 is a cross section of a fluid measuring apparatus 6 of the invention according to another preferred embodiment. The direction of the cross section in FIG. 7. is the same as that in FIG. 2. Compared with the fluid measuring apparatus 5, the difference is that the two cavities 122 and 122' of the fluid measuring apparatus 6 are disposed in series, that is, the outlet 126' of the cavity 122' is connected to the inlet 124 of the cavity 122. But filters 1242, 1242', 1262, and 1262' are still disposed at the outlets 126 and 126' and the inlets 124 and 124'. Similar to the discussion regarding the filters 1242 and 1262 of the fluid measuring apparatus 3, the aperture of the filter 1242' is larger than the aperture of the filter 1262'. In principle, the aperture of the filter 1262' of the outlet 126' of the cavity 122' is substantially equal to the aperture of the filter 1242 of the inlet 124 of the cavity 122, so that the cavities 122 and 122' accumulate the particles within continual ranges. In this case, the filters 1262' and 1242 could be integrated into a single filter. For some demand, such as a need to accumulate the particles within non-continual ranges, the aperture of the filter 1262' of the outlet 126' of the cavity 122' is larger than the aperture of the filter 1242 of the inlet 124 of the cavity 122. Wherein the range formed by the aperture of the filter 1262' and the aperture of the filter 1242 is then the unneeded range among the non-continual ranges. In this case the connecting channel between the cavity 122 and the cavity 122', which is between the filter 1262' and the filter 1242, will accumulate the particles within the unneeded range. It is added that the filters 1242, 1242', 1262, and 1262' are not necessarily disposed in both the cavities 122 and 122' of the fluid measuring apparatus 6 but are selectively disposed at the inlets 124 and 124' and the outlets 126 and 126' of the cavities 122 and 122' by request. Moreover, there are also two sets of the electrodes, namely the first electrode 142, the second electrode 144, the third electrode 142', and the forth electrode 144' disposed on the inner walls, wherein a first inspection room 151 is defined between the first electrode 142 and the second electrode 144, and a second inspection room 152 is defined between the third electrode 142' and the fourth electrode 144'; meanwhile, the first electrochromic device 16 is disposed on the collector 12 corresponding to the first inspection room 151, and a second electrochromic device 16' is disposed on the collector 12 corresponding to the second inspection room 152.

Figure 8:
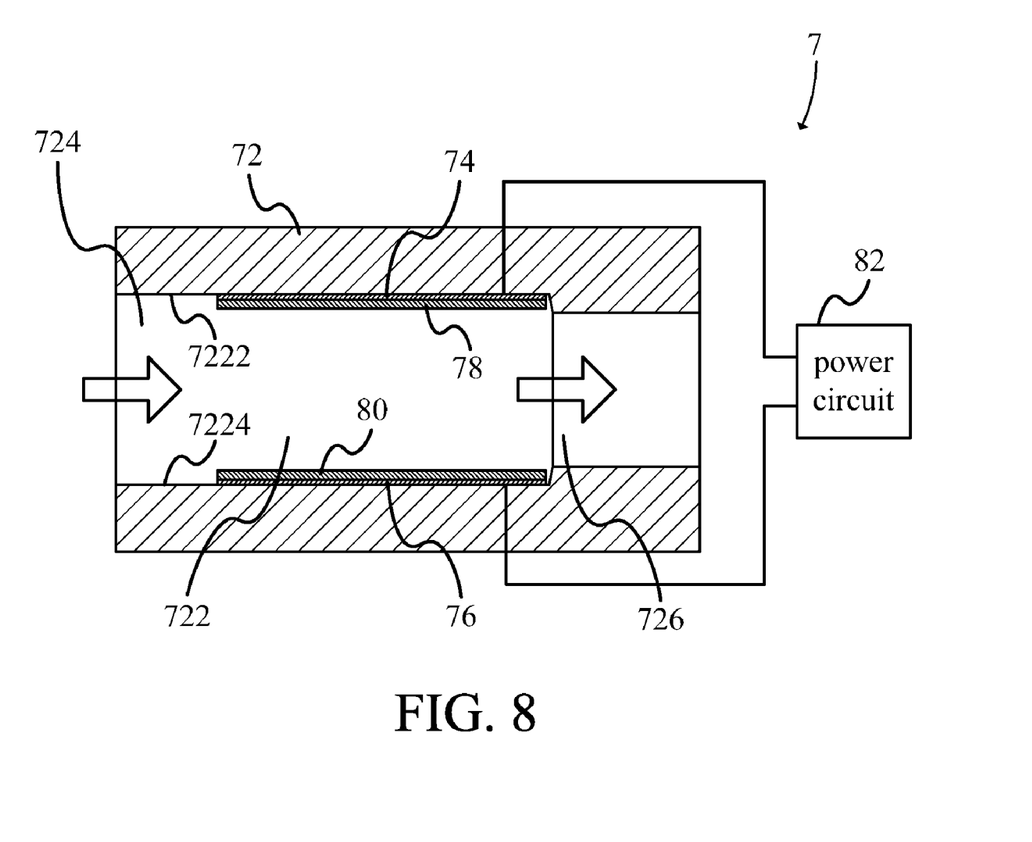
FIG. 8 is a cross section of a fluid measuring apparatus of the invention according to another preferred embodiment.

Please refer to FIG. 8. FIG. 8 is a cross section of a fluid measuring apparatus 7 of the invention according to another preferred embodiment. The direction of the cross section in FIG. 8 is the same as that in FIG. 2. The fluid measuring apparatus 7 of the invention includes a collector 72, a first electrode 74, a second electrode 76, an electrochromic material 78, and an ion storage layer 80. The collector 72 includes a cavity 722, an inlet 724, and an outlet 726. The cavity 722 includes a first inner wall 7222 and a second inner wall 7224. The first electrode 74 is disposed on the inner wall 7222. The second electrode 76 is disposed on the inner wall 7224. The electrochromic material 78 is disposed on the first electrode 74. The ion storage layer 80 is disposed on the second electrode 76. An electrolytic solution containing particles flows through the inlet 724 into the cavity 722 and flows out through the outlet 726. The hollow arrow in FIG. 8 indicates the flowing of the electrolytic solution. A power circuit 82 is connected to the first electrode 74 and the second electrode 76 and supplies power. When there is a voltage difference between the first electrode 74 and the second electrode 76 and current flows through, the ion stored in the ion storage layer 80 passes through the electrolytic solution into the electrochromic material 78 and then reacts with the electrochromic material 78 so that the color of the electrochromic material 78 changes. If there are enough ions in the electrolytic solution for reacting with the electrochromic material 78, the ion storage layer 80 could be omitted. Because the allowable magnitude of the current flowing through the first electrode 74 and the second electrode 76 is influenced by the concentration of the electrolytic solution flowing though between the first electrode 74 and the second electrode 76. When there is a voltage difference between the first electrode 74 and the second electrode 76 and the concentration of the electrolytic solution flowing through between the first electrode 74 and the second electrode 76 varies, the color of the electrochromic material 78 will get changed accordingly.

In order to easily observe the color change of the electrochromic material 78 from the outside of the fluid measuring apparatus 7, the collector 72 and the first electrode 74 could be made of transparent material or be hollowed partially. However, the strength issue of the fluid measuring apparatus 7 is needed to be considered. Furthermore, the descriptions regarding the components denoted in the same names, the optional components (such as filters), the manufacturing method, the disposition of several cavities, the disposition of several sets of electrodes in the same cavity, etc., in the above embodiments, can be applied to the fluid measuring apparatus 7 of the preferred embodiment, which is not described any more.

It is added that the electrochromic material is categorized into two categories, i.e, deoxidization coloration and oxidization coloration. The deoxidization coloration includes $WO_3$ (blue), $TiO_2$ (gray green), and $MoO_3$ (blue); the oxidization coloration includes $Ir(OH)_x$ (black), $Ni(OH)_x$ (dark blue), and Prussian Blue. Besides, there is deoxidization-oxidization coloration, such as polyaniline of polymeric material. Because it has at least two oxidized-deoxidized states, it has a multiple electrochromic property, and the range of the color change may be from transparent yellow, green, dark blue to black. Besides, there are other similar materials of deoxidization-oxidization coloration, such as $V_2O_5$, $CoO_x$, $Rh_2O_3$, and so on. All of the above-mentioned electrochromic materials can be applied to the invention, but the invention is not limited to this. In addition, because the electrochromic material may be either deoxidization coloration or oxidization coloration, the polarities of the electrochromic devices 16 and 16' need to be connected correspondingly. And, the electrochromic material 78 also needs to be disposed on the first electrode 74 or the second electrode 76 correspondingly based on the above consideration.

As described above, the fluid measuring apparatus of the invention utilizes that the change of the electrical property due to the change of the concentration of the fluid between the electrodes in the collector directly leads to the color change of the electrochromic material, so as to estimate the quantity of the particles in the fluid. The acquired estimation is not limited to the quantity of the particles; it could be the quantity per unit volume. Since the user faces the colors which are easily identified by human eyes, not current values, even without following fluorescence and image analysis, the user could quickly make a judgment via the fluid measuring apparatus of the invention. Because the degree of the color change of the electrochromic material is relative to the concentration of the fluid, that is, the color of the electrochromic material has difference of depth, it is helpful for a user to estimate the quantity of the particles. And, a color table with color difference of depth is pasted on the collector, so the accuracy of the judgement by the user could be increased greatly. Furthermore, the fluid measuring apparatus with cavities arranged in series could perform counting the particles within different ranges of particle size at the same time interval, while the fluid measuring apparatus with cavities arranged in parallel could increase the counting capability at the same time interval. In addition, by configuring several inspection rooms disposed with corresponding electrochromic devices in series, the fluid measuring apparatus of the invention could also provide a colored-bar display effect, which is more conducive to the estimation of the quantity of the accumulated particles in the fluid. Namely, it is more helpful for the user to identify the scale that the series electrochromic devices utilize different electrochromic material with different colored-state colors.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A fluid measuring apparatus, comprising:
   a collector, comprising a first cavity, a first inlet, and a first outlet, the first cavity comprising a first inner wall and a second inner wall;
   a first sensing circuit, comprising a first electrode disposed on the first inner wall and a second electrode disposed on the second inner wall;
   a first electrochromic device, electrically connected to the first sensing circuit and positioned corresponding to the collector; and
   a power circuit, electrically connected to the first sensing circuit and the first electrochromic device;
   wherein when the first sensing circuit is enabled, a change in color of the first electrochromic device can be visually observed if a concentration of a fluid flowing through and between the first electrode and the second electrode varies.

2. The fluid measuring apparatus of claim 1, wherein the first electrochromic device is electrically connected to the first sensing circuit in parallel or in series.

3. The fluid measuring apparatus of claim 1, wherein the first electrochromic device is electrically connected to the first electrode and the second electrode in parallel.

4. The fluid measuring apparatus of claim 1, wherein the first electrochromic device is disposed on a surface of the collector, and the surface corresponds to the first cavity.

5. The fluid measuring apparatus of claim 1, further comprising a second sensing circuit and a second electrochromic device electrically connected to the second sensing circuit, wherein the second sensing circuit comprises a third electrode on the first inner wall and a fourth electrode on the second inner wall.

6. The fluid measuring apparatus of claim 5, wherein in the first cavity, a first inspection room is defined between the first electrode and the second electrode, a second inspection room is defined between the third electrode and the fourth electrode, the first electrochromic device is disposed on the collector corresponding to the first inspection room, and the second electrochromic device is disposed on the collector corresponding to the second inspection room.

7. The fluid measuring apparatus of claim 5, wherein the first electrochromic device has a first colored-state color, the second electrochromic device has a second colored-state color, and the first colored-state color is different to the second colored-state color.

8. The fluid measuring apparatus of claim 1, wherein the first inlet comprises a first aperture, the first outlet comprises a second aperture, and the first aperture is larger than the second aperture.

9. The fluid measuring apparatus of claim 8, wherein the first aperture and the second aperture are in nano-scale.

10. The fluid measuring apparatus of claim 8, wherein the first inlet comprises a filter comprising the first aperture.

11. The fluid measuring apparatus of claim 8, wherein the first outlet comprises a filter comprising the second aperture.

12. The fluid measuring apparatus of claim 8, further comprising a third sensing circuit, a third electrochromic device, a second cavity, a second inlet, and a second outlet, the third sensing circuit being electrically connected to the third electrochromic device, wherein the second cavity comprises a third inner wall and a fourth inner wall, the third sensing circuit comprises a fifth electrode on the third inner wall and a sixth electrode on the fourth inner wall, the second inlet comprises a third aperture, the second outlet comprises a fourth aperture, the third aperture is larger than the fourth aperture, and the fourth aperture is larger than the first aperture.

13. The fluid measuring apparatus of claim 12, wherein the second outlet is connected to the first inlet.

14. The fluid measuring apparatus of claim 1, wherein the first electrochromic device comprises an electrochromic material disposed on the first electrode, and the fluid is an electrolytic solution.

15. The fluid measuring apparatus of claim 14, wherein the electrolytic solution comprises an ion for generating an electrochemical reaction with the electrochromic material.

16. The fluid measuring apparatus of claim 14, further comprising an ion storage layer disposed on the second electrode for storing an ion for generating an electrochemical reaction with the electrochromic material.

17. The fluid measuring apparatus of claim 14, wherein the collector and the first electrode are transparent.

18. The fluid measuring apparatus of claim 14, wherein the first inlet comprises a first aperture, the first outlet comprises a second aperture, and the first aperture is larger than the second aperture.

19. The fluid measuring apparatus of claim 14, further comprising a power circuit, the power circuit being electrically connected to the first electrode and the second electrode.

* * * * *